(12) United States Patent
Tran et al.

(10) Patent No.: US 8,609,704 B2
(45) Date of Patent: Dec. 17, 2013

(54) METHOD FOR REDUCING ODOR IN PERSONAL CARE PRODUCTS

(75) Inventors: Thu-Ba Thi Tran, Willow Grove, PA (US); Janet Nadya Younathan, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 621 days.

(21) Appl. No.: 12/459,968

(22) Filed: Jul. 10, 2009

(65) Prior Publication Data

US 2010/0022606 A1 Jan. 28, 2010

Related U.S. Application Data

(60) Provisional application No. 61/135,883, filed on Jul. 24, 2008.

(51) Int. Cl.
| | |
|---|---|
| A01N 43/80 | (2006.01) |
| A61K 31/425 | (2006.01) |
| A01N 33/02 | (2006.01) |
| A61K 31/13 | (2006.01) |
| A01N 31/00 | (2006.01) |
| A61K 31/10 | (2006.01) |

(52) U.S. Cl.
USPC .................. 514/372; 514/663; 514/712

(58) Field of Classification Search
USPC .................................. 514/372, 712
See application file for complete search history.

(56) References Cited

U.S. PATENT DOCUMENTS

| | | | |
|---|---|---|---|
| 4,920,137 A | 4/1990 | Segall et al. | |
| 5,133,969 A * | 7/1992 | Sekikawa et al. | 424/416 |
| 5,599,827 A | 2/1997 | Gironda | |
| 5,603,866 A | 2/1997 | Segall et al. | |
| 6,159,999 A | 12/2000 | Yagi et al. | |
| 6,429,220 B1 * | 8/2002 | Yagi et al. | 514/372 |
| 7,145,058 B2 * | 12/2006 | Sandal et al. | 800/294 |
| 2007/0135319 A1 | 6/2007 | Wei et al. | |
| 2008/0194728 A1 | 8/2008 | Ashmore et al. | |

FOREIGN PATENT DOCUMENTS

| | | |
|---|---|---|
| CN | 1939254 | 4/2007 |
| EP | 1016656 | 7/2000 |
| JP | 3839859 | 7/1996 |

* cited by examiner

*Primary Examiner* — Layla Soroush
(74) *Attorney, Agent, or Firm* — Kenneth Crimaldi

(57) ABSTRACT

A personal care composition which contains 25-200 ppm of 2-methyl-4-isothiazolin-3-one and at least one hydroquinone radical scavenger, and a method for reducing odor arising in personal care compositions containing 2-methyl-4-isothiazolin-3-one.

5 Claims, No Drawings

METHOD FOR REDUCING ODOR IN PERSONAL CARE PRODUCTS

This application claims the benefit of priority under 35 U.S.C. §119(e) of U.S. Provisional Patent Application No. 61/135,883 filed on Jul. 24, 2008.

This invention relates to a method for reducing odor arising from personal care products containing low levels of 2-methyl-4-isothiazolin-3-one.

Under some environmental conditions, personal care products preserved with relatively low levels of certain 2-methyl-4-isothiazolin-3-one biocide emit an undesirable odor. This fact has not been recognized previously. Combinations of various biocides with hydroquinones have been disclosed in the prior art, but not in personal care products at low levels. For example, CN 1,939,254 discloses anti-ageing products containing hydroquinones and a preservative, which may be an isothiazolone biocide. However, the preservative level disclosed in this reference is extremely high, 0.1-0.2%.

The problem addressed by this invention is to provide a method for reducing odor from personal care products containing relatively low levels of 2-methyl-4-isothiazolin-3-one.

STATEMENT OF THE INVENTION

The present invention is directed to a personal care composition comprising: (a) 25-200 ppm 2-methyl-4-isothiazolin-3-one; and (b) 50-2000 ppm of at least one hydroquinone radical scavenger.

One embodiment of the invention is a method for reducing odor arising from a personal care composition. The method comprises adding to the personal care composition: (a) 25-200 ppm 2-methyl-4-isothiazolin-3-one; and (b) 50-2000 ppm of at least one hydroquinone radical scavenger.

DETAILED DESCRIPTION OF THE INVENTION

"MIT" is 2-methyl-4-isothiazolin-3-one, also referred to by the name 2-methyl-3-isothiazolone. All percentages are by weight (wt %) and all temperatures in ° C., unless specified otherwise. The following abbreviations are used throughout the specification: ppm=parts per million by weight (weight/weight).

Combinations of the listed radical scavengers may be used, with or without additional stabilizers. Hindered phenol radical scavengers suitable for use in this invention include, e.g., 2,5-di-tert-butyl-1,4-hydroquinone; 2-tert-butyl-1,4-hydroquinone; 2,6-di-tert-butyl-4-hydroxytoluene; 2,6-di-tert-butyl-4-methoxyphenol; tert-butyl-4-hydroxyanisole; 2,5-bis-(2,4-dimethylphenyl)hydroquinone; propyl 3,4,5-trihydroxybenzoate; 2-(1,1-dimethylethyl)-1,4-benzenediol; 4-tert-butylcatechol; 4-butylresorcinol; 4-hydroxyanisole; 4-(1-phenylethyl)resorcinol; 2,5-di-tert-pentyl-1,4-hydroquinone; pyrocatechol; and 1,2,4-trihydroxybenzene. Preferred stabilizers include 2,5-di-tert-butyl-1,4-hydroquinone and 2-tert-butyl-1,4-hydroquinone.

A personal care composition is a formulation containing at least one active ingredient, and intended for application to human skin. Suitable active ingredients include but are not limited to sunscreening actives (UV absorbers), moisturizing actives such as moisturizing oils, cleansing actives for personal care, detergent actives for personal care, vitamins, folic acid derivatives, exfoliating agents, deodorizing actives, fragrance actives, topical medicament actives for personal care, cosmetic agents for personal care, hair conditioners, facial care products, body washes, infrared (IR)-absorbing materials for personal care, acne medications and combinations thereof. In some embodiments of the invention, the personal care compositions and formulations are of four basic compositions: oil dispersions, oil-in-water emulsions, water-in-oil emulsions and solutions from one or more organic solvents. Personal care formulations typically are prepared by combining the active ingredients, an oil base, optionally including an aqueous phase, and optional additives. Additional information regarding personal care formulations may be found in "The Chemistry and Manufacture of Cosmetics, Vol. II—Formulating, third ed., Mitchell L. Schlossman, editor, 1988, Allured Publishing Corporation.

Preferably, the hydroquinone radical scavenger(s) is present in the personal care formulation at a total level of at least 75 ppm, alternatively at least 100 ppm; alternatively at least 200 ppm, alternatively at least 400 ppm. In some embodiments of the invention the level of hydroquinone radical scavenger(s) is no greater than 1500 ppm, alternatively no greater than 1000 ppm, alternatively no greater than 800 ppm, alternatively no greater than 600 ppm. Preferably, the amount of hydroquinone radical scavenger is from two to ten times the amount of MIT, alternatively from three to eight times.

Preferably, the total level of MIT in the personal care formulation is at least 50 ppm, alternatively at least 50 ppm, alternatively at least 75 ppm. In some embodiments of the invention, the MIT level is no greater than 150 ppm, alternatively no greater than 125 ppm, alternatively no greater than 110 ppm, alternatively no greater than 100 ppm. In some embodiments of the invention, the MIT used in the personal care formulation contains less than 1% 5-chloro-2-methyl-4-isothiazolin-3-one (CMIT), alternatively less than 0.5%, alternatively less than 0.4%, alternatively less than 0.3%, alternatively less than 0.2%, alternatively less than 0.1%.

The hydroquinone radical scavenger can be added at any point during the preparation of the personal care formulation in any form (e.g., as an emulsion, dispersion, dry powder, paste or liquid).

Odor problems arising from MIT in personal care formulations often arise in the presence of at least one of an unsaturated aldehyde, an unsaturated ester, an unsaturated ketone and an unsaturated alcohol. Sources of such compounds include, e.g., fragrances, plant extracts (e.g., yerba mate, olive oil, and tea extracts, including white tea extract), and impurities in components of personal care formulations.

The invention claimed is:

1. A personal care composition comprising:
   (a) 50-150 ppm 2-methyl-4-isothiazolin-3-one;
   (b) 50-1000 ppm of at least one hydroquinone radical scavenger selected from the group consisting of 2,5-di-tert-butyl-1,4-hydroquinone; 2-tert-butyl-1,4-hydroquinone; 2,5-bis-(2,4-dimethylphenyl)hydroquinone; 2,5-di-tert-pentyl-1,4-hydroquinone; and 1,2,4-trihydroxybenzene; and
   (c) one or more plant extracts.

2. The composition of claim 1 in which said plant extracts comprise at least one of an unsaturated aldehyde, an unsaturated ester, an unsaturated ketone and an unsaturated alcohol.

3. The composition of claim 1 which is a cream, lotion or ointment.

4. The composition of claim 2 in which said at least one hydroquinone radical scavenger is selected from the group consisting of 2,5-di-tert-butyl-1,4-hydroquinone and 2-tert-butyl-1,4-hydroquinone.

5. The composition of claim 4 comprising one or more tea extracts.

* * * * *